United States Patent
Eberl et al.

(10) Patent No.: US 10,209,255 B2
(45) Date of Patent: Feb. 19, 2019

(54) METHOD FOR IDENTIFYING A BACTERIAL INFECTION

(71) Applicant: University College Cardiff Consultants Limited, Cardiff (GB)

(72) Inventors: Matthias Eberl, Cardiff (GB); Nicholas Topley, Cardiff (GB); Chan-Yu Lin, Taipei (TW)

(73) Assignee: UNIVERSITY COLLEGE CARDIFF CONSULTANTS LIMITED, Cardiff, South Glamorgan (GB)

( * ) Notice: Subject to any disclaimer, the term of this patent is extended or adjusted under 35 U.S.C. 154(b) by 58 days.

(21) Appl. No.: 14/775,738

(22) PCT Filed: Mar. 11, 2014

(86) PCT No.: PCT/GB2014/050720
§ 371 (c)(1),
(2) Date: Sep. 14, 2015

(87) PCT Pub. No.: WO2014/140558
PCT Pub. Date: Sep. 18, 2014

(65) Prior Publication Data
US 2016/0025725 A1    Jan. 28, 2016

(30) Foreign Application Priority Data

Mar. 14, 2013 (GB) .................. 1304626.3

(51) Int. Cl.
| | |
|---|---|
| *G01N 33/554* | (2006.01) |
| *G01N 33/569* | (2006.01) |
| *C12Q 1/04* | (2006.01) |
| *G01N 33/68* | (2006.01) |

(52) U.S. Cl.
CPC ......... *G01N 33/56972* (2013.01); *C12Q 1/04* (2013.01); *G01N 33/6863* (2013.01); *G01N 33/6869* (2013.01); *G01N 2333/525* (2013.01); *G01N 2333/54* (2013.01); *G01N 2333/545* (2013.01); *G01N 2333/5428* (2013.01); *G01N 2333/70514* (2013.01); *G01N 2333/70532* (2013.01)

(58) Field of Classification Search
None
See application file for complete search history.

(56) References Cited

PUBLICATIONS

Ebrel et al. PloS vol. 5, issue 2, Feb. 2009.*
Search Report for British patent application No. GB1304626.3 dated Sep. 11, 2013.
International Search Report and Written Opinion for International application No. PCT/GB2014/050720 dated Aug. 20, 2014.
Martin S. Davey et al: "Human Neutrophil Clearance of Bacterial Pathogens Triggers Anti-Microbial [gamma] [delta] T Cell Responses in Early Infection", PloS Pathogens, vol. 7, No. 5, May 12, 2011 (May 12, 2011).
Dratwa M et al: "Treatment of gram-negative peritonitis with aztreonam in patients undergoing continuous ambulatory peritoneal dialysis.", Reviews of Infectious Diseases May-Jun. 1991, A X,P A vol. 13 Suppl 7, May 1991 (May 1991), pp. S645-S647.
Matthias Eberl et al: "A Rapid Crosstalk of Human [gamma] [delta] T Cells and Monocytes Drives the Acute Inflammation in Bacterial Infections", PloS Pathogens, vol. 5, No. 2, Feb. 20, 2009 (Feb. 20, 2009), p. e1000308.
Lin Cy et al: "Pathogen-specific local immune fingerprints diagnose bacterial infection in peritoneal dialysis patients", Journal of the American Society of Nephrology, Williams and Wilkins, Baltimore, MD, vol. 24, No. 12, Dec. 1, 2013 (Dec. 1, 2013), pp. 2002-2009.
Wesch D et al: "Regulation of cytokine production by [gamma] [delta] T cells", Current Medicinal Chemistry Anti-Inflammatory & Anti-Allergyagents, Bentham Science Publishers, Hilversum, NL, vol. 4, No. 2, Apr. 1, 2005 (Apr. 1, 2005), pp. 153-160.
A. G. Cuenca et al: "Critical Role for CXC Ligand 10/CXC Receptor 3 Signaling in the Murine Neonatal Response to Sepsis", Infection and Immunity, vol. 79, No. 7, Jul. 1, 2011 (Jul. 1, 2011) pp. 2746-2754.

* cited by examiner

*Primary Examiner* — Jana A Hines
*Assistant Examiner* — Khatol S Shahnan Shah
(74) *Attorney, Agent, or Firm* — King & Schickli, PLLC

(57) ABSTRACT

Method for identifying a bacterial infection The present application concerns a method for identifying the nature of a bacterial infection from a peritoneal sample, in particular, whether it is a Gram-negative or Gram-positive infection, based upon the determination of one or more cellular and/or humoral markers in a sample.

6 Claims, 5 Drawing Sheets

METHOD FOR IDENTIFYING A BACTERIAL INFECTION

This application is the national stage of international patent application no. PCT/GB2014/050720 filed on Mar. 11, 2014 which in turn claims priority from British application GB1304626.3 filed on Mar. 14, 2013, the disclosures of which are incorporated herein by reference in their entirety.

TECHNICAL FIELD

The present application relates to at least one method for identifying the nature of a bacterial infection from a peritoneal sample, and in particular whether the infection is caused by Gram-positive and/or Gram-negative bacteria. More specifically, said method involves identifying the relative amount of one or more cellular and/or humoral markers in said sample. Further, said invention concerns a method of treatment involving the use of said method, ideally to allow informed decision making in the selection of treatment regimens and/or of monitoring successful treatment outcome.

BACKGROUND

Bacterial infection remains a leading cause of morbidity and mortality worldwide, not least due to the unprecedented spread of antibiotic-resistant pathogens. Moreover, effective infection control is hampered by the poor performance of standard diagnostics and hence inadequate choices are being made about the use of effective treatments. This alarming situation is posing an enormous challenge for clinical practice, public healthcare and biomedical research.

Current diagnosis and treatment of suspected infections depends largely on the positive identification of the likely microbiological pathogen, a concept that was introduced by Robert Koch more than a century ago but has not changed since then. Positive identification of the causative pathogen of a bacterial infection is not only crucial to guide and refine patient management with respect to the choice of antibiotic treatment, but it also provides us with important clues as to the underlying inflammatory mechanisms and how these can be manipulated to help resolve infection.

Presently, detection and characterisation of infectious organisms requires classical microbiological culture techniques, spectrometry based assays and/or highly complex nucleic acid identification methods. Mohan et al, 2011 describe the combined use of nucleic acid detection and immunoassay detection e.g. "oligonucleotide probes optimized for hybridization at 37° C. to facilitate integration with the immunoassay" to diagnose urinary tract infections [5]. Podsiadly et al, 2005 describe detection of levels of specific Chlamydia pneumoniae IgM, IgG and IgA serum antibodies to diagnose urinary infections [6]. These latter assays are considered unreliable.

Moreover, pathogen identification is significantly hampered by the inherent delay associated with a reliance on conventional culture techniques. It often takes 2 days, or even longer, before the results are available to the treating doctor, to enable specific and targeted therapy. In some diseases, such as tuberculosis, this can take up to two months. Most importantly, in many cases bacteria cannot be cultured by traditional methods, meaning that the cause underlying the patient's clinical symptoms remains unknown.

Typically, infection is only apparent when significant clinical symptoms appear. Effective and specific therapeutic intervention depends on early detection and identification of the causative organism. Conventionally, patient management is determined on the basis of symptoms, initial clinical findings, and other basic laboratory markers of inflammation such as C-reactive protein. This approach is often suboptimal being too general and lacking in specificity. Increased specificity is generally only attained by microbiological identification and antibiotic sensitivity testing, and this can be associated with delay in the optimal management of the infection. The tendency to use broad spectrum antibiotics to cover a number of possible aetiological agents encourages the development of other serious problems such as *C. difficile* infection, and also bacterial resistance. Thus, there is a clear clinical need to achieve earlier and better detection and characterisation of the infection in order to 1) improve patient outcomes; 2) improve the use of specific anti-infectives; and 3) reduce antimicrobial resistance and the development of other serious infections. Technologies capable of achieving this should enhance the patient experience, and ensure a more sustainable, cost-effective approach to patient management.

Peritoneal dialysis (PD) is a treatment for patients with severe chronic kidney disease. Therapy involves the introduction of specialised dialysis fluids into the peritoneal cavity, via a Tenckhoff tube, with the aim of removing toxins that accumulate on kidney failure by diffusion and also water by the osmotic gradient created by the fluid. Both processes occur contemporaneously across the semipermeable peritoneal membrane. Infection of the glucose rich dialysis fluid, leading to peritonitis, is a major complication of PD that has significant morbidity and mortality implications.

Peritonitis can have a detrimental effect on both short and long term patient health. In the short term, severe peritonitis episodes can result in the need to immediately remove the Tenckhoff tube and, therefore, treatment failure. In the long term, recurrent or severe peritonitis can result in thickening (fibrosis) of the peritoneal membrane and significant alterations in membrane permeability/function that lead to treatment failure. Early recognition of the onset of peritonitis coupled with rapid investigation, diagnosis, and effective treatment is imperative for successful outcome. Identification of the causative micro-organism using standard techniques can be difficult due to the relatively low bacterial numbers and the length of time required to culture them (often many days). This leads to the phenomenon of 'culture negative' peritonitis, i.e. all clinical and laboratory parameters confirm the diagnosis but no organism is ever identified, in 0-50% of cases [3]. Consequently, given the delays in micro-organism confirmation, all patients are started on dual antibiotic treatment to cover both Gram-positive and Gram-negative bacteria. Only when (and if) the organism is identified is the antibiotic regimen refined. If the PD fluid specimen remains culture negative, then the patient is required to undergo prolonged dual, broad spectrum, antibiotic treatment.

As mentioned above, whilst molecular tests that identify microorganisms in biological fluids are available, they often suffer from a lack of specificity, unacceptably high rates of false positivity and the frequent identification of non-pathogenic species that are due to contamination of the sample or asymptomatic carriage.

It follows from the above that point-of-care methods that direct therapy, especially in cases where organism species or virulence is a determinant of outcome, are urgently required.

The present disclosure relates to methods of rapid diagnosis of infection in peritoneal disease. In the present study we performed a detailed immunological and microbiological analysis in PD patients on the first day of presentation with acute peritonitis. Key to this technology is the discovery that the induction of complex cellular and humoral immune responses rapidly follows exposure of the immune system to an infectious agent. Surprisingly, this response is apparent within hours of the exposure and can be measured in the draining effluent of peritoneal dialysis patients with acute clinical symptoms, at the time of presenting with a characteristic but not diagnostic 'cloudy bag'. As such, these results have far-reaching implications for differential diagnosis of patients with suspected infections and may help guide patient management through faster biomarker-based diagnostics, better predictive risk modelling and improved targeting of a therapy and its ultimate efficacy.

SUMMARY

According to a first aspect of the invention there is provided a method for identifying a Gram-negative bacterial infection in a peritoneal sample, which method comprises:
  (a) examining said peritoneal sample from an individual in order to determine the amount of $V\delta2^+$ T cells within the total T cell population of said sample, and;
  (b) where the amount of $V\delta2^+$ T cells within the total T cell population is increased relative to the amount of $V\delta2^+$ T cells within the total T cell population in a control sample from an individual not having a Gram-negative bacterial infection;
  (c) concluding that the individual from whom the peritoneal sample has been taken has a Gram-negative bacterial infection.

As will be appreciated by those skilled in the art, reference herein to Gram-negative bacterial infection concerns infection with a bacterium that does not retain crystal violet dye in the Gram staining protocol. Examples of Gram-negative bacteria include, but are not limited to, the genera *Acinetobacter, Aeromonas, Bacteroides, Bartonella, Bordetella, Brucella, Burkholderia, Campylobacter, Chlamydia, Chryseobacterium, Citrobacter, Enterobacter, Escherichia, Francisella, Fusobacterium, Haemophilus, Hafnia, Helicobacter, Klebsiella, Legionella, Moraxella, Morganella, Neisseria, Pantoea, Photobacterium, Proteus, Providencia, Pseudomonas, Salmonella, Serratia, Shigella, Stenotrophomonas, Veillonella, Vibrio, Yersinia.*

Reference herein to peritoneal sample refers to a sample of fluid from the abdominal cavity, including peritoneal effluent, typically from a PD patient, or tissue removed from the membrane lining the abdominal cavity (peritoneum).

Reference herein to a control sample from an individual not having a Gram-negative bacterial infection is reference to a sample that has been shown not to have a Gram-negative bacterial infection using any one or more conventional techniques for identifying same.

In a preferred embodiment of the invention examining said peritoneal sample from an individual in order to determine the amount of $V\delta2^+$ T cells within the total T cell population of said sample may be undertaken directly or indirectly. A direct examination of said peritoneal sample from an individual in order to determine the amount of $V\delta2^+$ T cells within the total T cell population of said sample is undertaken by measuring the amount of $V\delta2^+$ T cells within the total T cell population of said sample. An indirect examination of said peritoneal sample from an individual in order to determine the amount of $V\delta2^+$ T cells within the total T cell population of said sample is undertaken by measuring the amount of other T cells within the total T cell population of said sample, measuring the total T cell population of said sample and then performing a subtraction to determine the amount of $V\delta2^+$ T cells within the total T cell population of said sample. Alternatively, indirect examination of said peritoneal sample from an individual in order to determine the amount of $V\delta2^+$ T cells within the total T cell population of said sample is undertaken by assaying for surrogate markers, i.e. markers that are representative of $V\delta2^+$ T cells, e.g. by measuring $V\gamma9^+$ T cells, pan-$\gamma\delta^+$ T cells, pan-$\alpha\beta^-$ (alpha/beta negative T cells) or $CD4^-CD8^-$ ("double-negative" or DN) T cells, where typically all or at least the majority of cells will be $V\delta2^+$ T cells. Those skilled in the art will appreciate the nature of the cells to look for in order to perform this indirect measurement.

Preferably, said peritoneal sample is fluid from the peritoneal space, which as appreciated by those skilled in the art, may be removed by numerous means such as, but not limited to, a needle and syringe. Alternatively, and more preferably, said sample may be obtained from peritoneal dialysate of those undergoing peritoneal dialysis treatment i.e., ideally, peritoneal effluent.

The control sample ideally refers to a sample taken from the same site as the test but from an individual not infected (so-called "stable patients").

An individual not having a Gram-negative bacterial infection may or may not have symptoms of infection such as elevated temperature, abdominal pain or discomfort or cloudy effluent or, in the case of a patient undergoing PD, the presence of a non-cloudy dialysate when viewed by the eye. Additionally, or alternatively, said individual not having an infection is identified by being negative for a bacterial infection, particularly a Gram-negative infection, when exposed to a culture test to try and grow and so identify a bacterial infection or when exposed to other conventional techniques to identify a bacterial infection.

As known by those skilled in the art, $V\delta2^+$ T cells are a distinct subset of $CD3^+$ T cells that are characterized by positive expression of the TCR-$V\delta2$ chain and typically by co-expression of the $V\gamma9$ chain ($V\gamma2$ according to an alternative nomenclature). These $V\gamma9/V\delta2$ T cells are commonly found in peripheral blood and inflamed tissues and play an important role in immune processes during microbial infections.

In yet a further preferred embodiment of the invention at least one additional study is undertaken to determine the amount of anyone or more of the following in the peritoneal sample relative to said control:
  d) IL-10;
  e) IL-1$\beta$;
  f) TNF-$\alpha$;
  g) $V\delta2^+$ T cells expressing HLA-DR; and/or
  h) monocytes within the total leukocyte population expressing CD86; and where the amount of any one or more of d)-g) is increased relative to the amount of same in said control or in the case of h) is decreased relative to the amount of same in said control, concluding that the individual from whom the peritoneal sample has been taken has a Gram-negative bacterial infection.

In a preferred embodiment of the invention said method of the invention may be performed using steps ac) and any one or more of steps b)-f) including any preferred combination thereof.

Interleukin 10 (IL-10 or IL10), also known as human cytokine synthesis inhibitory factor (CSIF), is an anti-inflammatory cytokine. In humans, IL-10 is known to have pleiotropic effects in immunoregulation and inflammation.

IL-1β is a member of the interleukin 1 cytokine family produced by activated immune cells, and is known to be an important mediator of the inflammatory response.

TNF-α is a member of the TNF cytokine family and produced by many different cell types, and is known to be an important mediator of the inflammatory response.

HLA-DR is a MHC class H cell surface receptor encoded by the human leukocyte antigen complex, and is known to be up-regulated in response to signaling. Specifically, in response to an infection, bacterial antigens bind a DR molecule and are presented to T-cell receptors found on T-helper cells.

Cluster of Differentiation 86 (also known as CD86 and B7-2) is a protein expressed on antigen-presenting cells that provides co-stimulatory signals necessary for T cell activation and survival.

According to a second aspect of the invention there is provided a method for identifying a Gram-positive bacterial infection in a peritoneal sample, which method comprises:
  (a) examining said peritoneal sample from an individual in order to determine the amount of CXCL10 and;
  (b) where the amount of CXCL10 is increased relative to the amount of CXCL10 in a control sample from an individual not having a Gram-positive bacterial infection;
  (c) concluding that the individual from whom the peritoneal sample has been taken has a Gram-positive bacterial infection.

CXCL10 is a cytokine belonging to the CXC chemokine family, and is secreted by several cell types in response to IFN-γ. These cell types include monocytes, T cells, endothelial cells and fibroblasts. CXCL10 is known to be increased in response to many infections.

As will be appreciated by those skilled in the art, reference herein to Gram-positive bacterial infection concerns an infection with a bacterium that does retain crystal violet dye in the Gram staining protocol. Examples of Gram-positive bacteria include, but are not limited to, the genera *Actinomyces, Bacillus, Clostridium, Corynebacterium, Enterococcus, Lactobacillus, Lactococcus, Leuconostoc, Listeria, Micrococcus, Mycobacterium, Peptostreptococcus, Propionibacterium, Staphylococcus, Streptococcus, Streptomyces*.

Reference herein to peritoneal sample refers to a sample of fluid from the abdominal cavity, including peritoneal effluent, typically from a PD patient, or tissue removed from the membrane lining the abdominal cavity (peritoneum).

Reference herein to a control sample from an individual not having a Gram-positive bacterial infection is reference to a sample that has been shown not to have a Gram-positive bacterial infection using any one or more conventional techniques for identifying same.

Preferably, said peritoneal sample is fluid from the peritoneal space, which as appreciated by those skilled in the art, may be removed by numerous means such as, but not limited to, a needle and syringe. Alternatively, and more preferably, said sample may be obtained from peritoneal dialysate of those undergoing peritoneal dialysis treatment i.e., ideally, peritoneal effluent.

The control sample ideally refers to a sample taken from the same site as the test but from an individual not infected (so-called "stable patients").

An individual not having a Gram-positive bacterial infection may or may not have symptoms of infection such as elevated temperature, abdominal pain or discomfort or cloudy effluent or, in the case of a patient undergoing PD, the presence of a non-cloudy dialysate when viewed by the eye. Additionally, or alternatively, said individual not having an infection is identified by being negative for a bacterial infection, particularly a Gram-positive infection, when exposed to a culture test to try and grow and so identify a bacterial infection or when exposed to other conventional techniques to identify a bacterial infection.

In yet a further preferred embodiment of the second aspect of the invention at least one additional study is undertaken to determine the amount of any one or more of the following in the peritoneal sample relative to said control:
  (d) Vδ2$^+$ T cells within the total T cell population;
  (e) total numbers of CD4$^+$ T cells; or
  (f) IL-22;
and where the amount of d) is decreased relative to the amount of same in said control and/or the amount of e) and/or f) is increased relative to the amount of same in said control,
  concluding that the individual from whom the peritoneal sample has been taken has a Gram-positive bacterial infection.

CD4$^+$ T helper cells area sub-division of white blood cells that are an essential part of the human immune system, characterized by cell surface expression of the CD4 glycoprotein. CD4 is a co-receptor that assists the T cell receptor (TCR) in communicating with an antigen-presenting cell.

IL-22 is a cytokine that is a member of a group of cytokines called the IL-10 family or IL-10 superfamily, which are known to be mediators of cellular inflammatory responses. IL-22 is produced by activated dendritic cells and T cells and initiates innate immune responses against bacterial pathogens.

In a preferred embodiment of the invention said method of the second aspect of the invention may be performed using step a) and any one or more of steps d)-f) including any preferred combination thereof.

According to a third aspect of the invention, or a preferred embodiment of the first and/or second aspect of the invention, said method for identifying a Gram-negative bacterial infection is carried out after, or alternatively prior to, said method for identifying a Gram-positive bacterial infection, or vice versa. Alternatively, said methods may be carried out simultaneously.

According to a fourth aspect of the invention there is provided a method for treating an individual suffering from a bacterial infection as identified by any one of more of the above methods, which further comprises administering to said individual a therapeutic for treating a Gram-negative and/or Gram-positive bacterial infection depending upon the nature of the bacterial infection identified by said above methods.

According to a preferred embodiment of the fourth aspect of the invention, said method for treating an individual suffering from a bacterial infection further comprises periodically repeating any one of more of the above methods for identifying a Gram-negative and/or Gram-positive infection and, where it is concluded that said individual is still infected, continuing to administer said therapeutic or changing the therapeutic regimen.

According to a preferred embodiment of the fourth aspect of the invention, said therapeutic includes, but is not limited to, an antibiotic such as those belonging to the families of penicillins and beta-lactamase inhibitors, cephalosporins, macrolides and lincosamines, quinolones and fluoroquinolones, carbapenems, monobactams, am inoglycosides, tetracyclines, sulfonamides, rifampin, oxazolidonones, and derivatives thereof.

As will be appreciated by those skilled in the art, said antibiotic may be broad spectrum and efficacious against both Gram-positive and/or Gram-negative bacteria, such as but not limited to, all beta-lactams including beta-lactam/inhibitor combinations, all macrolides, all tetracyclines, all aminoglycosides, all polymixins, all quinolones, all glycopeptides, all lincosamides, all streptomycin derivatives, and all antibiotics not covered by generic classes such as chloramphenicol, rifampicin, fosfomycin, fosmidomycin, nitrofurantoin, metronidazole, daptomycin, quinupristin, linezolid, telavancin, mupirocin, and folate synthesis inhibitors, as well as structural analogues and derivates thereof.

More ideally, said antibiotic is specific and efficacious against Gram-negative bacteria, such as but not limited to, all beta-lactams including beta-lactam/inhibitor combinations, all macrolides, all tetracyclines, all aminoglycosides, all polymixins, all quinolones, all lincosamides, all streptomycin derivatives, and all antibiotics not covered by generic classes such as chloramphenicol, rifampicin, fosfomycin, fosmidomycin, nitrofurantoin, metronidazole, and folate synthesis inhibitors, as well as structural analogues and derivates thereof.

Alternatively, said antibiotic is specific and efficacious against Gram-positive bacteria, such as but not limited to, all beta-lactams including beta-lactam/inhibitor combinations, all macrolides, all tetracyclines, all aminoglycosides, all quinolones, all glycopeptides, all lincosamides, all streptomycin derivatives, and all antibiotics not covered by generic classes such as chloramphenicol, rifampicin, fosfomycin, fosmidomycin daptomycin, quinupristin, linezolid, telavancin, mupirocin, and folate synthesis inhibitors, as well as structural analogues and derivates thereof.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The Invention will now be described in greater detail with reference to the Examples below and to the drawings in which.

Figure 1:
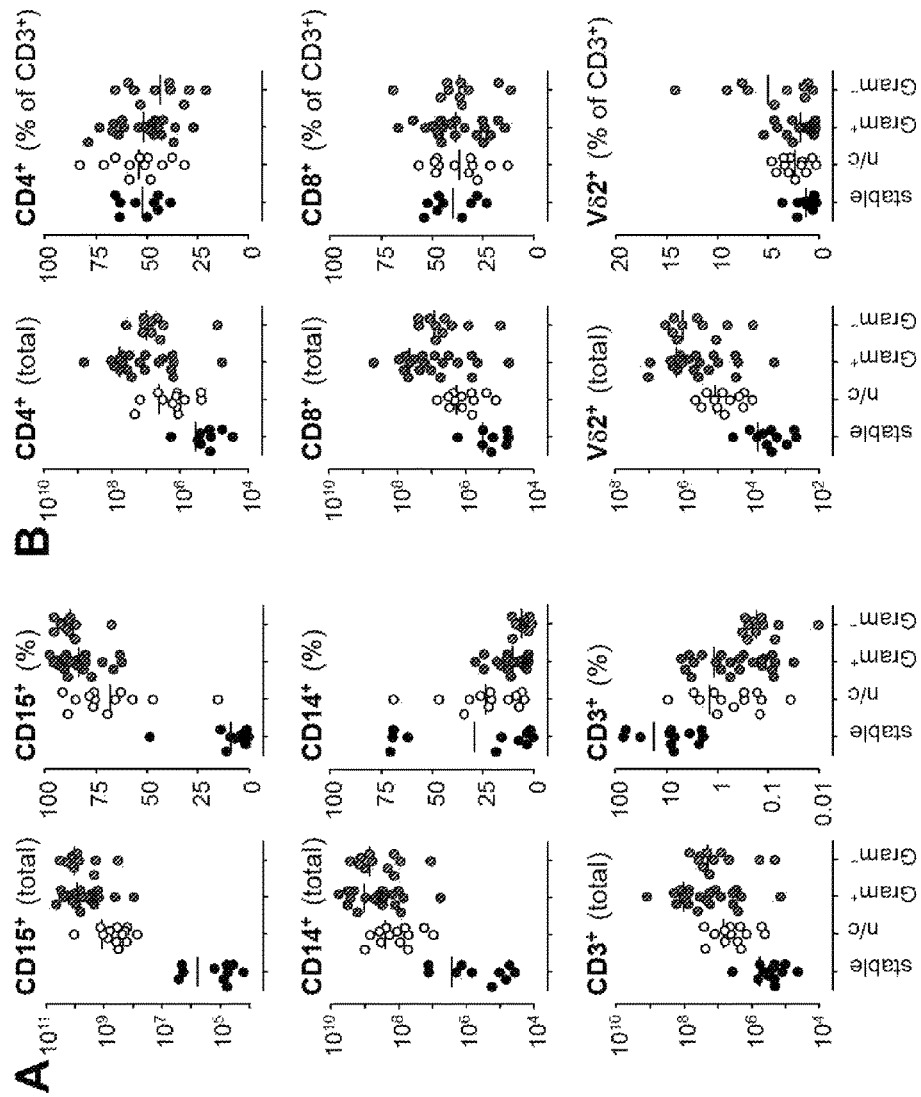
FIG. 1A shows total number and relative frequency (%) of peritoneal neutrophils (CD15$^+$), monocytes/macrophages (CD14$^+$) and T cells (CD3$^+$) in stable and infected PD patients on day 1 of acute peritonitis. Infected patients were grouped according to the microbiological culture results into patients with culture-negative (n/c) or confirmed Gram-positive or Gram-negative infection. Data points represent individual patients, horizontal lines mean values per group.
FIG. 1B shows total number and proportion of helper T cells (CD4$^+$), cytotoxic T cells (CD8$^+$) and γδ T cells (Vδ2$^+$) within the peritoneal CD3$^+$ T cell population in stable and infected PD patients on day 1 of acute peritonitis. Infected patients were grouped according to the microbiological culture results into patients with culture-negative (n/c) or confirmed Gram-positive or Gram-negative infection. Data points represent individual patients, horizontal lines mean values per group.

Table 1. Immunological biomarkers in stable patients and patients presenting with a 'cloudy bag' on day 1 (mean±SEM). n.s., not significant.

Table 2. Immunological biomarkers in patients presenting with a 'cloudy bag' on day 1, depending on the absence or presence of a confirmed Gram-negative infection (mean±SEM). n.s., not significant.

Table 3. Ability of immunological biomarkers to discriminate between Gram-negative and non-Gram-negative episodes of peritonitis on day 1.

Table 4. Prediction of Gram-negative infection on the first day of presentation with acute peritonitis.

Table 5. Immunological biomarkers showing diagnostic significance for prediction of Gram-negative episodes of peritonitis on day 1.

Table 6. Immunological biomarkers in patients presenting with a 'cloudy bag' on day 1, depending on the absence or presence of a confirmed Gram-positive infection (mean±SEM). n.s., not significant.

Table 7. Ability of immunological biomarkers to discriminate between Gram-positive and non-Gram-positive episodes of peritonitis on day 1.

Table 8. Prediction of Gram-positive infection on the first day of presentation with acute peritonitis.

Table 9. Immunological biomarkers showing diagnostic significance for prediction of Gram-positive episodes of peritonitis on day 1.

Table 10. Biomarkers of potential diagnostic value in patients presenting with a 'cloudy bag' on day 1, depending on the microbiological culture results.

DETAILED DESCRIPTION

Materials and Methods

Patients

We recruited 52 adult patients who were receiving PD at the University Hospital of Wales, Cardiff, UK, and were admitted on day 1 of acute peritonitis between 1 Sep. 2008 and 31 Jan. 2012. 15 stable patients with no infection in the previous 3 months were included in this study as non-infected controls. Sampling of PD effluent was approved by the South East Wales Local Ethics Committee (04WSE04/27), and conducted according to the principles expressed in the Declaration of Helsinki. All patients provided written informed consent. Diagnosis of acute peritonitis was based on the presence of abdominal pain and cloudy peritoneal effluent with >100 WBC/mm$^3$. Infections were grouped into culture-negative, Gram-positive and Gram-negative episodes, according to the result of the microbiological analysis of the effluent, which was conducted at the central diagnostic laboratories of the University Hospital of Wales.

Flow Cytometry

Peritoneal cells were acquired on an eight-color FACSCanto II (BD Biosciences) and analyzed with FloJo (Tree Star), using monoclonal antibodies against CD3 (UCHT1), CD4 (SK3), CD8 (RPA-T8), CD15 (HI98), CD69 (FN50), CD86 (2331-FUN1), HLA-DR (L234) and TCR-Vδ2 (B6.1) from BD Biosciences; CD14 (61D3) from eBioscience; and TCR-Vγ9 (Immu360) from Beckman Coulter, together with appropriate isotype controls. Leukocyte populations were identified based on their appearance in side scatter and forward scatter area/height, exclusion of live/dead staining (fixable Aqua; Invitrogen), and surface staining: CD15$^+$ neutrophils, CD14$^+$ monocytes/macrophages and CD3$^+$ T cells. T cell subsets were identified as CD4$^+$ helper T cells, CD8$^+$ cytotoxic T cells and Vδ2$^+$ γδ T cells.

ELISA

Cell-free peritoneal effluents were analyzed for TNF-α, GM-CSF, IFN-γ, IL-1β, IL-2, IL-6, IL-10, IL-12p70, CXCL8 and sIL-6R on a SECTOR Imager 6000 (Meso Scale Discovery). IL-17A, IL-22, CXCL10 and MMP-3 (R&D Systems) as well as TGF-β1 (eBioscience) were measured in duplicate on a Dynex MRX II reader, using conventional ELISA kits.

Statistical Analysis

Statistical analyses were performed using SPSS 16.0 and GraphPad Prism 4.0 software. All variables were tested for normal distributions using the Kolmogorov-Smirnov test. Differences between patient groups were analyzed using Student's t-tests for normally distributed data or Mann-Whitney U-tests for non-parametric data. Categorical data were tested using the Chi-square test. Predictive biomarkers were assessed using univariate analysis; statistically significant ($p<0.05$) variables from the univariate analysis were included in a multivariate analysis. Multiple logistic regression analyses were conducted based on forward and/or backward elimination of data, as indicated in the tables. Discrimination was assessed using AUROC curves and compared using non-parametric approaches; AUROC analyses were also used to calculate cut-off values, sensitivity and specificity. Cumulative survival curves as a function of time were generated using the Kaplan-Meier approach and compared using the log rank test. All statistical tests were two-tailed; differences were considered statistically significant as indicated in the figures and tables: *, $p<0.05$; , $p<0.01$; *, $p<0.001$.

Results

Acute Episodes of Peritonitis are Associated with Severe Peritoneal Inflammation Patients presenting with acute peritonitis were characterized by a significant peritoneal influx of immune cells, predominantly CD15$^+$ neutrophils, CD14$^+$ monocytes/macrophages and CD3$^+$ T cells (Table 1). This was true for culture-negative episodes of peritonitis as well as cases of confirmed infection by Gram-negative or Gram-positive bacteria (FIG. 1). While peritoneal leukocytes in stable patients comprised mainly of monocytes/macrophages and T cells, acute peritonitis was dominated by a massive recruitment of neutrophils, at times reaching >95% of all peritoneal cells and >10$^{11}$ cells in total. Detailed flow cytometrical analyses of the peritoneal leukocyte population revealed further striking changes in the composition of the local immune cell infiltrate in patients with acute peritonitis. As such, there was a preferential increase in the frequency of Vδ2$^+$ T cells within the T cell population in acute peritonitis, while the percentages of CD4$^+$ and CD8$^+$ T cells remained virtually unchanged (Table 1).

Figure 2:
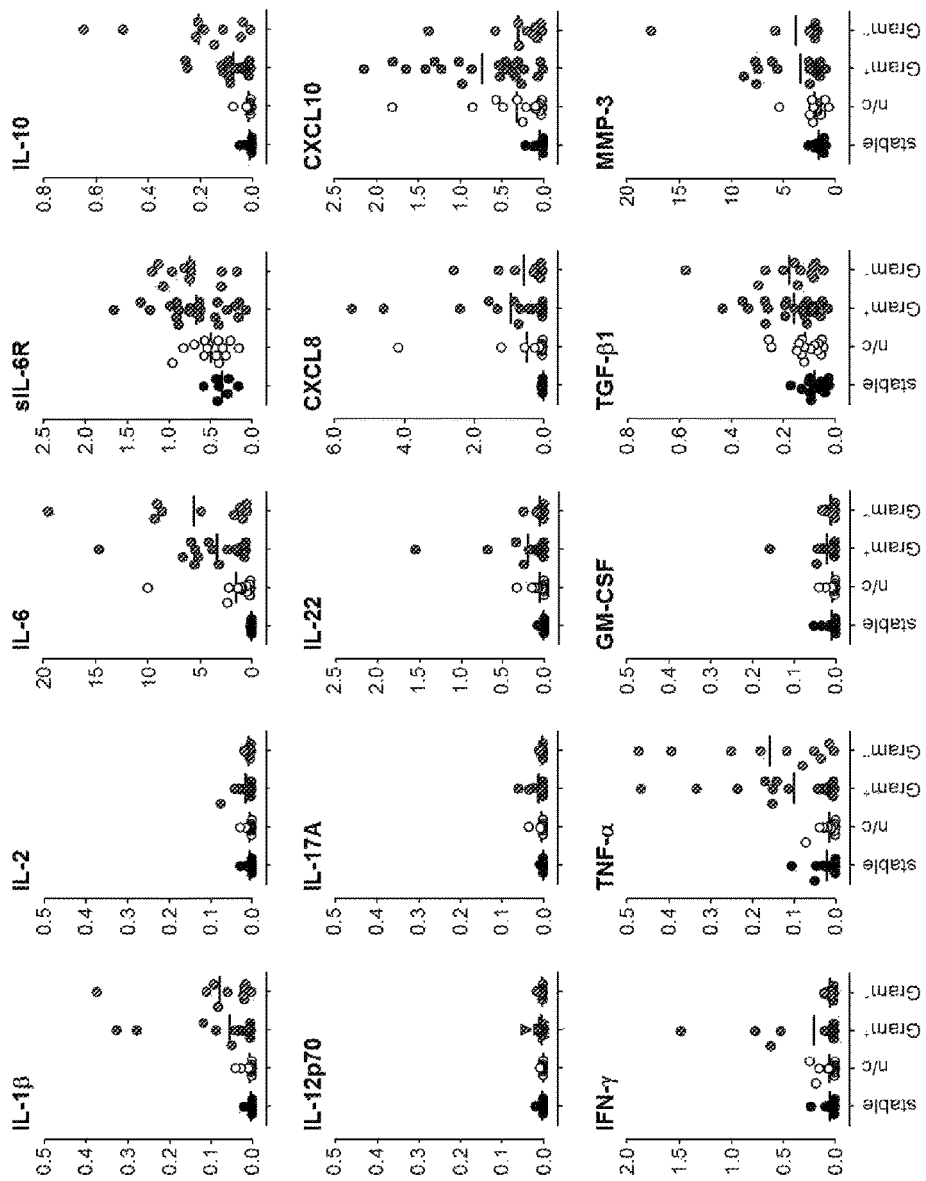
FIG. 2. Relates to humoral indicators. Peritoneal levels (in ng/ml) of IL-1β, IL-2, IL-6, sIL 6R, IL-10, IL-12p70, IL-17A, IL-22, CXCL8, CXCL10, IFN-γ, TNF-α, GM-CSF, TGF-β1 and MMP-3 in stable and infected PD patients on day 1 of acute peritonitis. Infected patients were grouped according to the microbiological culture results into patients with culture-negative (n/c) or confirmed Gram-positive or Gram-negative infection. Data points represent individual patients, horizontal lines mean values per group.

Soluble mediators significantly increased in acute peritonitis included interleukin-1β (IL-1β), IL-6, soluble IL-6 receptor (sIL-6R), IL-10, IL-22, CXCL8, CXCL10, tumour necrosis factor-α (TNF-α), transforming growth factor-β (TGF-β) and matrix metalloproteinase-3 (MMP-3); at the same time levels of cytokines such as IL-2, IL-12p70, IL-17 and granulocyte/macrophage colony-stimulating factor (GM-CSF) were not elevated above baseline or, in the case of interferon-γ (IFN-γ), not significantly (FIG. 2, Table 1). Taken together, these measurements identify a broad range of humoral and cellular biomarkers that indicate acute inflammatory responses in PD patients, some of which might be of diagnostic value.

Distinct Immune Fingerprints in Patients with Gram-Negative Infections have Diagnostic Potential on Day 1

Figure 3:
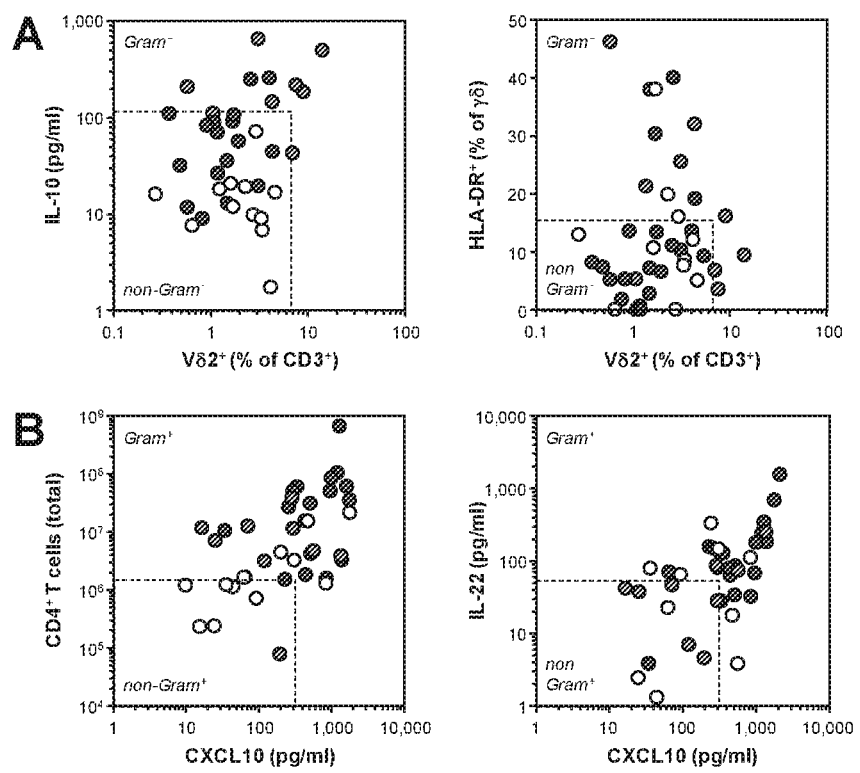
FIG. 3A presents examples of immunological biomarkers in patients presenting with a 'cloudy bag' on day 1, depending on the microbiological culture results, showing discrimination between Gram-negative and non-Gram-negative infections. Data points represent individual episodes (white, culture-negative; blue, confirmed Gram-positive infection; red, confirmed Gram-negative infection. Dashed lines indicate calculated cut-off values for positive or negative discrimination.
FIG. 3B presents examples of immunological biomarkers in patients presenting with a 'cloudy bag' on day 1, depending on the microbiological culture results, showing discrimination between Gram-positive and non-Gram-positive infections. Data points represent individual episodes (white, culture-negative; blue, confirmed Gram-positive infection; red, confirmed Gram-negative infection. Dashed lines indicate calculated cut-off values for positive or negative discrimination.
Figure 4:
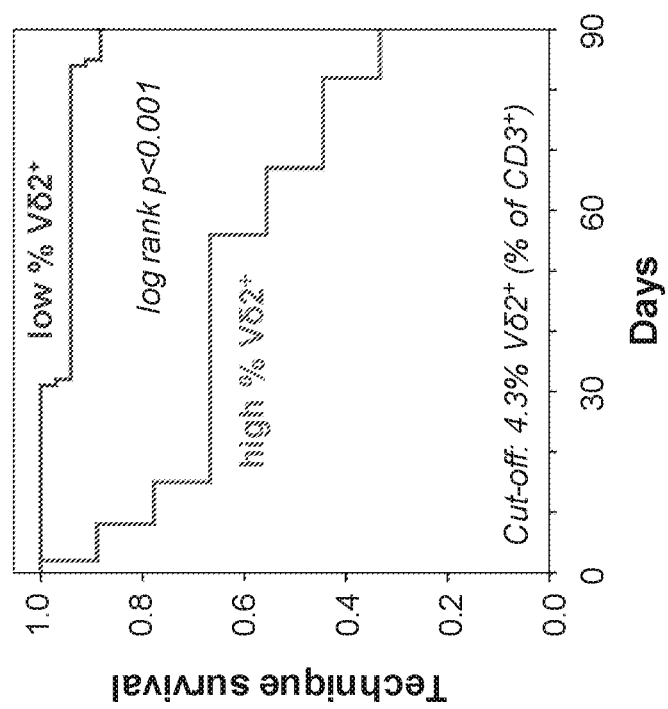
FIG. 4. Kaplan-Meier plot showing cumulative technique survival of patients with acute peritonitis, depending on the frequency of Vδ2$^+$ T cells among all peritoneal T cells on day 1. The cut-off value was determined by ROC analysis. AUROC for 30th technique failure prediction: 0.917±0.048, 95% confidence interval: 0.823-1.000, Youden Index: 0.85, sensitivity: 100%, specificity: 85%. The statistical difference between the two curves was analysed by log rank test.

We next tested whether pathogen-specific immune fingerprints exist that could predict infections by certain groups of bacteria. Given the importance of Gram-negative bacteria in the clinic and their association with worse outcomes we initially concentrated on the prediction of Gram-negative infections. Amongst all patients presenting with a cloudy bag on day 1, patients with confirmed Gram-negative infections displayed larger numbers of infiltrating neutrophils and consequently lower proportions of monocytes/macrophages and T cells than the rest of the patients, i.e. individuals with culture-negative or Gram-positive infections (Table 2). Within the T cell population, Vδ2⁺ T cells were significantly increased and expressed higher levels of the activation marker HLA-DR in Gram-negative infections. In turn, peritoneal monocytes/macrophages expressed lower levels of CD86 in Gram-negative infections, compared to the rest of the patients. Inflammatory markers significantly increased in Gram-negative infections included IL-1β, IL-10 and TNF-α (FIG. 3A; Table 2). AUROC calculations identified the combination of Vδ2⁺ T cell frequencies and peritoneal levels of IL-10 as excellent discriminator to predict Gram-negative infections (Table 3). This combination also had the highest overall correctness, with 100% sensitivity and 93% specificity for the correct prediction of Gram-negative peritonitis (Table 4). The prognostic value of the proportion of monocytes/macrophages amongst all cells (≤10.7%) and their expression of CD86 (≤67.9%), the frequency of Vδ2⁺ T cells with the T cell population (≥6.3%) and their expression of HLA-DR (≥16.1%), and peritoneal IL-10 levels (≥110.1 pg/ml) were all confirmed by univariate analyses. Multivariate analysis of these parameters identified the Vδ2⁺ T cell frequency as independent prognostic biomarker for the prediction of Gram-negative peritonitis in all patients presenting with a cloudy bag on day 1 (Table 5). As Gram-negative infections are associated with higher rates of technique failure and mortality, we finally tested whether the peritoneal Vδ2⁺ T cell frequency has any indirect predictive power as to clinical outcome from episodes of acute peritonitis. As shown in FIG. 4, there was a clear difference between patients with a relatively low and a relatively high proportion of peritoneal Vδ2⁺ T cells on the day of presentation. While patients with Vδ2⁺ T cell levels below the cut-off value of 4.3% had very low rates of technique failure over the following 3 months, patients with Vδ2⁺ T cell levels higher than 4.3% had a significantly elevated risk of technique failure, confirming Vδ2⁺ T cells as having both diagnostic and prognostic value in PD patients with acute peritonitis.

Distinct Immune Fingerprints in Patients with Gram-Positive Infections have Diagnostic Potential on Day 1

In an analogous way, we next attempted to identify predictors of Gram-positive infections. Amongst all patients presenting with a cloudy bag on day 1, patients with confirmed Gram-positive infections displayed larger numbers of infiltrating CD4⁺ and CD8⁺ T cells than the rest of the patients, i.e. individuals with culture-negative or Gram-negative infections (Table 6), while the proportion of Vδ2⁺ T cells within the T cell population was significantly lower in Gram-positive infections. Inflammatory markers significantly increased in Gram-positive infections included IL-22 and CXCL10 (FIG. 3B; Table 6). AUROC calculations identified the combination of CXCL10 (≥301.2 pg/ml) and IL-22 levels (≥54.3 pg/ml) and Vδ2⁺ T cell frequencies (≥2.7%) as excellent discriminator to predict Gram-positive infections (Table 7). This combination also had the highest overall correctness, with 89% sensitivity and 67% specificity for the correct prediction of Gram-positive peritonitis. In turn, CXCL10 levels (≥301.2 pg/ml) combined with total CD4⁺ T cell counts (≥15.2·10⁶) had a sensitivity of only 53% yet at a specificity of 95% for the prediction of Gram-positive peritonitis (Table 8). CD4⁺ T cell counts as well as Vδ2⁺ T cell frequencies and CXCL10 levels had prognostic value as confirmed by univariate analyses. Multivariate analysis of these parameters alone and in combination identified the combination of CD4⁺ T cell counts and CXCL10 levels as independent biomarker for the prediction of Gram-positive peritonitis in all patients presenting with a cloudy bag on day 1 (Table 9).

Figure 5:
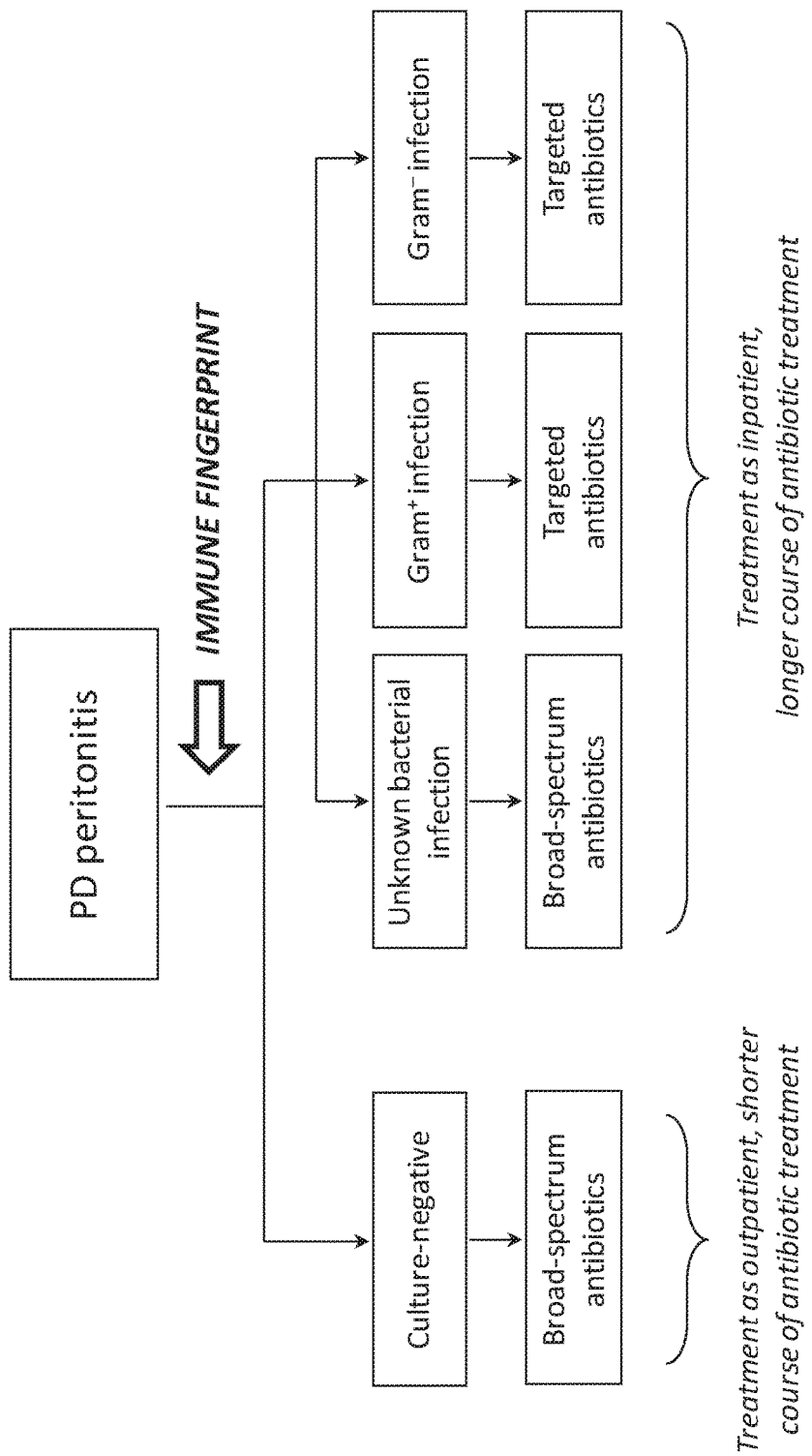
FIG. 5. Flow chart of proposed PD peritonitis treatment as guided by immune fingerprint-based diagnostic tests, depending on the test result.

Taken together, our findings indicate that immune fingerprint-based diagnostic tests are able to guide treatment of patients with acute infections (FIG. 5). Depending on the test result, patients might be diagnosed as having a culture-negative episode (i.e. no bacterial infection present) of peritonitis that is associated with relatively benign outcome. Such patients might benefit from shorter course treatments as outpatients (and might not need any antibiotics at all if the episode is of non-infectious origin). Patients diagnosed with Gram-positive or Gram-negative infections might benefit from better targeted therapy, and especially in the case of Gram-negative infections that are associated with high rates of technique failure and mortality, from close monitoring and improved management. In the case of unknown bacterial infection, patients might receive the conventional treatment with broad-spectrum antibiotics.

SUMMARY

Our research highlights the importance of combining humoral and cellular parameters to establish accurate Immune fingerprints'. Particularly promising humoral and cellular parameters in the definition of disease-specific immune fingerprints include local levels of IL-1β, IL-10, IL-22, TNF-α and CXCL10, as well as the relative proportion of neutrophils and monocytes/macrophages among total peritoneal cells and the frequency of γδ T cells within the peritoneal T cell population (Table 10).

Consequently, it has therefore been shown that immune fingerprints of bacterial infections exist, and that characteristic immunological biomarkers have the potential to distinguish and predict early bacterial infection and so direct appropriate modes of treatment.

REFERENCES

3. Fahim M, Hawley C M, McDonald S P, Brown F G, Rosman J B, Wiggins K J, Bannister K M, Johnson D W: Culture-negative peritonitis in peritoneal dialysis patients in Australia: predictors, treatment, and outcomes in 435 cases. Am J Kidney Dis 55: 690-697, 2010
5. Mohan R, Mach K E, Bercovici M, Pan Y, Dhulipala L, Wong P K, Liao J C: Clinical validation of integrated nucleic acid and protein detection on an electrochemical biosensor array for urinary tract infection diagnosis. PLoS One 6(10): e26846, 2011
6. Podsiadty E, Fracka B, Szmigielska A, Tylewska-Wierzbanowska S: Seroepidemiological studies of *Chlamydia pneumoniae* infections in 1-36 months old children with respiratory tract infections and other diseases in Poland. Pol J Microbiol. 54(3):215-9, 2005.

TABLE 1

Immunological biomarkers in stable patients and patients presenting with a 'cloudy bag' on day 1 (mean ± SEM).

|  | Stable PD | Cloudy bag | p |
| --- | --- | --- | --- |
| Gender (male/female) | 9/6 | 32/20 | n.s. |
| Age (years) | 60.4 ± 4.9 | 65.5 ± 2.0 | n.s. |
| Days on PD (days) | 1,058 ± 219.2 | 1,142 ± 131.1 | n.s. |
| Neutrophils (·10⁶) | 0.6 ± 0.3 | 7,048 ± 1,384 | *** |
| Monocytes (·10⁶) | 2.8 ± 1.5 | 753.9 ± 166.0 | *** |
| CD4⁺ T cells (·10⁶) | 0.3 ± 0.2 | 32.3 ± 15.7 | *** |
| CD8⁺ T cells (·10⁶) | 0.3 ± 0.2 | 24.5 ± 12.0 | *** |
| Vδ2⁺ T cells (·10⁶) | 0.01 ± 0.003 | 1.1 ± 0.4 | *** |

TABLE 1-continued

Immunological biomarkers in stable patients and patients presenting with a 'cloudy bag' on day 1 (mean ± SEM).

|  | Stable PD | Cloudy bag | p |
|---|---|---|---|
| Neutrophils (% of total) | 9.0 ± 4.2 | 80.3 ± 2.2 | *** |
| Monocytes (% of total) | 28.9 ± 9.4 | 12.9 ± 1.9 | n.s. |
| T cells (% of total) | 17.5 ± 6.8 | 1.0 ± 0.3 | *** |
| CD4+ (% of T cells) | 52.2 ± 3.3 | 50.6 ± 2.1 | n.s. |
| CD8+ (% of T cells) | 40.0 ± 3.8 | 37.6 ± 2.1 | n.s. |
| Vδ2+ (% of T cells) | 1.3 ± 0.3 | 2.9 ± 0.4 | * |
| IL-1β (pg/ml) | 3.7 ± 1.6 | 45.1 ± 12.6 | *** |
| IL-2 (pg/ml) | 6.2 ± 2.2 | 11.4 ± 2.1 | n.s. |
| IL-6 (pg/ml) | 37.1 ± 7.3 | 3,249 ± 623.6 | *** |
| sIL-6R (pg/ml) | 360.1 ± 50.8 | 639.6 ± 50.3 | ** |
| IL-10 (pg/ml) | 10.9 ± 3.8 | 85.6 ± 19.4 | *** |
| IL-12p70 (pg/ml) | 4.2 ± 1.5 | 4.5 ± 1.0 | n.s. |
| IL-17 (pg/ml) | 1.5 ± 1.0 | 6.7 ± 2.7 | n.s. |
| IL-22 (pg/ml) | 13.9 ± 7.7 | 121.8 ± 36.5 | ** |
| CXCL8 (pg/ml) | 18.1 ± 3.2 | 699.3 ± 191.7 | *** |
| CXCL10 (pg/ml) | 43.2 ± 22.5 | 514.1 ± 82.7 | *** |
| IFN-γ (pg/ml) | 52.7 ± 16.6 | 123.0 ± 39.7 | n.s. |
| TNF-α (pg/ml) | 21.8 ± 8.4 | 86.8 ± 18.8 | * |
| GM-CSF (pg/ml) | 11.3 ± 4.4 | 15.5 ± 3.8 | n.s. |
| MMP-3 (pg/ml) | 1,540 ± 184.9 | 3,029 ± 427.3 | ** | n.s., not significant.

TABLE 2

Immunological biomarkers in patients presenting with a 'cloudy bag' on day 1, depending on the absence or presence of a confirmed Gram-negative infection (mean ± SEM).

|  | Other | Gram-negative | p |
|---|---|---|---|
| Gender (male/female) | 25/15 | 7/5 | n.s. |
| Age (years) | 64.1 ± 2.4 | 70.1 ± 2.9 | n.s. |
| Days on PD (days) | 1,234 ± 156.2 | 899.3 ± 248.3 | n.s. |
| Neutrophils (·10$^6$) | 5,875 ± 1,580 | 10,779 ± 2,686 | * |
| Monocytes (·10$^6$) | 754.7 ± 206.1 | 751.1 ± 242.9 | n.s. |
| CD4+ T cells (·10$^6$) | 39.3 ± 20.5 | 9.9 ± 3.4 | n.s. |
| CD8+ T cells (·10$^6$) | 29.5 ± 15.6 | 8.6 ± 2.8 | n.s. |
| Vδ2+ T cells (·10$^6$) | 1.1 ± 0.4 | 1.1 ± 0.4 | n.s. |
| Neutrophils (% of total) | 78.1 ± 2.7 | 87.7 ± 2.3 | n.s. |
| Monocytes (% of total) | 15.1 ± 2.3 | 5.8 ± 1.0 | * |
| T cells (% of total) | 1.3 ± 0.3 | 0.2 ± 0.03 | * |
| CD4+ (% of T cells) | 52.7 ± 2.3 | 43.7 ± 4.6 | n.s. |
| CD8+ (% of T cells) | 37.8 ± 2.4 | 36.6 ± 5.0 | n.s. |
| Vδ2+ (% of T cells) | 2.0 ± 0.2 | 5.0 ± 1.4 | * |
| HLA-DR+ (% of γδT cells) | 10.8 ± 1.8 | 22.5 ± 4.7 | * |
| CD86+ (% of monocytes) | 72.6 ± 3.6 | 53.1 ± 7.2 | * |
| IL-1β (pg/ml) | 35.0 ± 12.5 | 79.5 ± 34.7 | * |
| IL-2 (pg/ml) | 12.2 ± 2.6 | 8.8 ± 1.9 | n.s. |
| IL-6 (pg/ml) | 2,561 ± 538.8 | 5,586 ± 1,942 | n.s. |
| sIL-6R (pg/ml) | 606.3 ± 57.6 | 751.4 ± 100.9 | n.s. |
| IL-10 (pg/ml) | 49.4 ± 10.6 | 208.6 ± 65.5 | ** |
| IL-12p70 (pg/ml) | 4.6 ± 1.3 | 4.1 ± 1.4 | n.s. |
| IL-17 (pg/ml) | 8.4 ± 3.7 | 2.4 ± 1.3 | n.s. |
| IL-22 (pg/ml) | 139.8 ± 45.9 | 56.8 ± 22.9 | n.s. |
| CXCL8 (pg/ml) | 742.6 ± 237.5 | 552.3 ± 257.8 | n.s. |
| CXCL10 (pg/ml) | 570.1 ± 97.7 | 306.9 ± 130.2 | n.s. |
| IFN-γ (pg/ml) | 144.5 ± 50.9 | 50.0 ± 11.6 | n.s. |
| TNF-α (pg/ml) | 65.3 ± 17.9 | 159.7 ± 51.8 | * |
| GM-CSF (pg/ml) | 16.6 ± 4.8 | 12.1 ± 3.6 | n.s. |
| MMP-3 (pg/ml) | 2,804 ± 359.2 | 3,765 ± 1,429 | n.s. | n.s., not significant.

TABLE 3

Ability of immunological biomarkers to discriminate between Gram-negative and non-Gram-negative episodes of peritonitis on day 1.

|  | AUROC ± SEM | 95% CI | p |
|---|---|---|---|
| For Gram-negative prediction | | | |
| Monocytes (% of total) | 0.745 ± 0.075 | 0.597-0.893 | * |
| Vδ2+ (% of T cells) | 0.710 ± 0.106 | 0.501-0.918 | * |
| HLA-DR+ (% of γδT cells) | 0.720 ± 0.097 | 0.530-0.911 | * |
| CD86+ (% of monocytes) | 0.740 ± 0.083 | 0.578-0.903 | * |
| IL-10 (pg/ml) | 0.803 ± 0.092 | 0.622-0.984 | ** |
| IL-1β (pg/ml) | 0.738 ± 0.086 | 0.569-0.907 | * |
| TNF-α (pg/ml) | 0.735 ± 0.091 | 0.557-0.914 | * |
| IL-10 + Vδ2+ | 0.976 ± 0.022 | 0.934-1.000 | *** |
| IL-10 + Vδ2+ + HLA-DR+ | 0.959 ± 0.031 | 0.899-1.000 | *** |
| IL-1β + IL-10 + TNF-α | 0.844 ± 0.077 | 0.693-0.995 | ** |

TABLE 4

Prediction of Gram-negative infection on the first day of presentation with acute peritonitis.

|  | Cut-off Point | Youden Index | Sensitivity (%) | Specificity (%) |
|---|---|---|---|---|
| For Gram-negative prediction | | | | |
| Monocytes (% of total) | 10.7 | 0.50 | 50 | 100 |
| Vδ2+ (% of T cells) | 6.3 | 0.46 | 46 | 100 |
| HLA-DR+ (% of γδT cells) | 16.1 | 0.48 | 64 | 84 |
| CD86+ (% of monocytes) | 67.9 | 0.47 | 74 | 73 |
| IL-10 (pg/ml) | 110.1 | 0.61 | 70 | 91 |
| IL-1β (pg/ml) | 14.0 | 0.55 | 90 | 65 |
| TNF-α (pg/ml) | 32.8 | 0.45 | 80 | 65 |
| IL-10 + Vδ2+ | 0.5 | 0.93 | 100 | 93 |
| IL-10 + Vδ2+ + HLA-DR+ | 0.5 | 0.78 | 100 | 78 |
| IL-1β + IL-10 + TNF-α | 2.5 | 0.61 | 70 | 91 |

TABLE 5

Immunological biomarkers showing diagnostic significance for prediction of Gram-negative episodes of peritonitis on day 1.

|  | β Coefficient | Standard error | Odds ratio (95% CI) | p |
|---|---|---|---|---|
| Univariate logistic regression | | | | |
| Monocytes (% of total) | −0.189 | 0.093 | 0.828 (0.690-0.994) | * |
| Vδ2+ (% of T cells) | 0.385 | 0.159 | 1.469 (1.075-2.008) | * |
| HLA-DR+ (% of γδT cells) | 0.072 | 0.029 | 1.075 (1.014-1.139) | * |
| CD86+ (% of monocytes) | −0.037 | 0.016 | 0.964 (0.934-0.995) | * |
| IL-10 | 0.012 | 0.005 | 1.012 (1.003-1.022) | * |
| Multivariate logistic regression (backward) | | | | |
| Vδ2+ (% of T cells) | 0.571 | 0.246 | 1.770 (1.093-2.866) | * |
| Constant | −4.591 | 1.376 | 0.010 | — |

TABLE 6

Immunological biomarkers in patients presenting with a 'cloudy bag' on day 1, depending on the absence or presence of a confirmed Gram-positive infection (mean ± SEM).

|  | Other | Gram-positive | p |
|---|---|---|---|
| Gender (male/female) | 17/10 | 15/10 | n.s. |
| Age (years) | 68.2 ± 2.4 | 62.4 ± 3.1 | n.s. |
| Days on PD (days) | 1,058 ± 167.9 | 1,266 ± 213.9 | n.s. |

TABLE 6-continued

Immunological biomarkers in patients presenting with a 'cloudy bag' on day 1, depending on the absence or presence of a confirmed Gram-positive infection (mean ± SEM).

|  | Other | Gram-positive | p |
|---|---|---|---|
| Neutrophils (·10⁶) | 5,604 ± 1,610 | 8,623 ± 2,293 | n.s. |
| Monocytes (·10⁶) | 477.2 ± 128.0 | 1,056 ± 309.1 | n.s. |
| CD4⁺ T cells (·10⁶) | 6.8 ± 1.9 | 60.2 ± 32.2 | ** |
| CD8⁺ T cells (·10⁶) | 4.9 ± 1.5 | 46.1 ± 24.5 | * |
| Vδ2⁺ T cells (·10⁶) | 0.6 ± 0.2 | 1.6 ± 0.7 | n.s. |
| Neutrophils (% of total) | 77.2 ± 3.8 | 83.7 ± 2.1 | n.s. |
| Monocytes (% of total) | 15.4 ± 3.3 | 10.3 ± 1.5 | n.s. |
| T cells (% of total) | 0.9 ± 0.4 | 1.1 ± 0.3 | n.s. |
| CD4⁺ (% of T cells) | 49.3 ± 3.2 | 51.9 ± 2.9 | n.s. |
| CD8⁺ (% of T cells) | 36.6 ± 3.0 | 38.6 ± 3.1 | n.s. |
| Vδ2⁺ (% of T cells) | 3.6 0.7 | 1.8 0.3 | * |
| HLA-DR⁺ (% of γδT cells) | 17.2 ± 3.0 | 10.3 ± 2.1 | n.s. |
| CD86⁺ (% of monocytes) | 62.9 ± 5.3 | 73.0 ± 4.1 | n.s. |
| IL-1β (pg/ml) | 37.3 ± 16.0 | 54.5 ± 20.1 | n.s. |
| IL-2 (pg/ml) | 7.6 ± 1.4 | 16.0 ± 4.0 | n.s. |
| IL-6 (pg/ml) | 3,204 ± 970.8 | 3,303 ± 753.0 | n.s. |
| sIL-6R (pg/ml) | 607.2 ± 60.0 | 674.8 ± 83.2 | n.s. |
| IL-10 (pg/ml) | 96.5 ± 33.1 | 72.5 ± 16.0 | n.s. |
| IL-12p70 (pg/ml) | 3.1 ± 0.7 | 6.2 ± 2.0 | n.s. |
| IL-17 (pg/ml) | 3.7 ± 1.9 | 12.1 ± 6.5 | n.s. |
| IL-22 (pg/ml) | 55.8 ± 16.8 | 193.8 ± 71.8 | ** |
| CXCL8 (pg/ml) | 504.3 ± 199.9 | 933.3 ± 346.0 | n.s. |
| CXCL10 (pg/ml) | 316.6 ± 88.8 | 738.4 ± 131.4 | ** |
| IFN-γ (pg/ml) | 55.5 ± 12.7 | 204.0 ± 83.6 | n.s. |
| TNF-α (pg/ml) | 76.0 ± 25.8 | 99.7 ± 28.5 | n.s. |
| GM-CSF (pg/ml) | 10.1 ± 2.2 | 22.0 ± 7.8 | n.s. |
| MMP-3 (pg/ml) | 2,760 ± 658.1 | 3,336 ± 532.7 | n.s. | n.s., not significant.

TABLE 7

Ability of immunological biomarkers to discriminate between Gram-positive and non-Gram-positive episodes of peritonitis on day 1.

|  | AUROC ± SEM | 95% CI | p |
|---|---|---|---|
| For Gram-positive prediction | | | |
| CD4⁺ T cells (·10⁶) | 0.741 ± 0.079 | 0.587-0.895 | ** |
| CD8⁺ T cells (·10⁶) | 0.723 ± 0.083 | 0.561-0.885 | * |
| Vδ2⁺ (% of T cells) | 0.699 ± 0.079 | 0.543-0.854 | * |
| CXCL10 (pg/ml) | 0.744 ± 0.075 | 0.596-0.891 | ** |
| IL-22 (pg/ml) | 0.736 ± 0.074 | 0.591-0.881 | ** |
| CXCL10 + Vδ2⁺ | 0.821 ± 0.066 | 0.691-0.951 | *** |
| CXCL10 + IL-22 + Vδ2⁺ | 0.816 ± 0.069 | 0.681-0.951 | ** |
| CXCL10 + CD4⁺ | 0.797 ± 0.073 | 0.653-0.941 | ** |
| CXCL10 + IL-22 | 0.794 ± 0.068 | 0.661-0.926 | ** |

TABLE 8

Prediction of Gram-positive infection on the first day of presentation with acute peritonitis.

|  | Cut-off Point | Youden Index | Sensitivity (%) | Specificity (%) |
|---|---|---|---|---|
| For Gram-positive prediction | | | | |
| CD4⁺ T cells (·10⁶) | 15.2 | 0.46 | 55 | 91 |
| CD8⁺ T cells (·10⁶) | 7.8 | 0.46 | 60 | 86 |
| CXCL10 (pg/ml) | 301.2 | 0.49 | 77 | 72 |
| IL-22 (pg/ml) | 54.3 | 0.39 | 73 | 67 |
| CXCL10 + IL-22 + Vδ2⁺ | 1.5 | 0.561 | 89 | 67 |
| CXCL10 + Vδ2⁺ | 0.5 | 0.524 | 100 | 52 |
| CXCL10 + CD4⁺ | 1.5 | 0.48 | 53 | 95 |
| CXCL10 + IL-22 | 0.5 | 0.49 | 91 | 55 |

TABLE 8-continued

Prediction of Gram-positive infection on the first day of presentation with acute peritonitis.

|  | Cut-off Point | Youden Index | Sensitivity (%) | Specificity (%) |
|---|---|---|---|---|
| For non-Gram-positive prediction | | | | |
| Vδ2⁺ (% of T cells) | 2.7 | 0.375 | 57 | 81 |

TABLE 9

Immunological biomarkers showing diagnostic significance for prediction of Gram-positive episodes of peritonitis on day 1.

|  | βCoefficient | Standard error | Odds ratio (95% CI) | p |
|---|---|---|---|---|
| Univariate logistic regression | | | | |
| CD4⁺ T cells (·10⁶) | 0.062 | 0.026 | 1.064 (1.011-1.119) | * |
| CD8⁺ T cells (·10⁶) | 0.077 | 0.035 | 1.080 (1.008-1.156) | * |
| Vδ2⁺ (% of T cells) | −0.388 | 0.185 | 0.679 (0.472-0.976) | * |
| CXCL10 (pg/ml) | 0.002 | 0.001 | 1.002 (1.000-1.003) | * |
| Multivariate logistic regression (forward) | | | | |
| CXCL10 + CD4⁺ | 1.972 | 0.597 | 7.186 (2.229-23.170) | ** |
| Constant | −1.543 | 0.581 | 0.214 | — |

TABLE 10

Biomarkers of potential diagnostic value in patients presenting with a 'cloudy bag' on day 1, depending on the microbiological culture results.

|  | Culture-negative | Culture-positive | Gram-positive | Gram-negative |
|---|---|---|---|---|
| Monocytes (% of total) | ≥19.1 | <19.1 |  | <10.7 |
| CD4⁺ T cells (·10⁶) |  |  | ≥15.2 |  |
| Vδ2⁺ (% of T cells) |  |  | ≤2.7 | ≥6.3 |
| HLA-DR⁺ (% of γδT cells) |  |  |  | ≥16.1 |
| CD86⁺ (% of monocytes) |  |  |  | <67.9 |
| IL-1β (pg/ml) | <4.1 | ≥4.1 |  | ≥14.0 |
| IL-10 (pg/ml) | <23.3 | ≥23.3 |  | ≥110.1 |
| IL-22 (pg/ml) |  |  | ≥54.3 |  |
| CXCL10 (pg/ml) |  |  | ≥301.2 |  |
| TNF-α (pg/ml) | <19.5 | ≥19.5 |  | ≥32.8 |

The invention claimed is:
1. A method for treating an individual suffering from a peritoneal Gram-negative bacterial infection, comprising:
(a) obtaining a peritoneal sample from the individual;
(b) examining said peritoneal sample in order to determine an amount of Vδ2⁺ T cells within the total T cell population of said sample and an amount of IL-10 in said sample;
(c) where the amount of Vδ2⁺ T cells within the total T cell population is increased relative to an amount of Vδ2⁺ T cells within the total T cell population in a control sample from an individual not having a Gram-negative bacterial infection and the amount of IL-10 is increased relative to an amount of IL-10 in a control sample from an individual not having a Gram-negative bacterial infection, concluding that the individual from whom the peritoneal sample has been taken has a Gram-negative bacterial infection; and
(d) administering to the individual a therapeutic for treating the peritoneal Gram-negative bacterial infection.

2. The method of claim 1, further including periodically repeating the step of identifying the Gram-negative infection and, where it is concluded that said individual is still suffering from the peritoneal Gram-negative bacterial infection, continuing to administer to said individual the therapeutic for treating the peritoneal Gram-negative bacterial infection.

3. The method according to claim 2 wherein said therapeutic is selected from the group consisting of: penicillins, beta-lactamase inhibitors, cephalosporins, macrolides, lincosamides, quinolones, fluoroquinolones, carbapenems, monobactams, aminoglycosides, tetracyclines, sulfonamides, oxazolidonones, all beta-lactams including beta-lactam/inhibitor combinations, polymixins, glycopeptides, streptomycins, and all antibiotics not covered by generic classes such as chloramphenicol, rifampicin, fosfomycin, fosmidomycin, nitrofurantoin, metronidazole, daptomycin, quinupristin, linezolid, telavancin, mupirocin, and folate synthesis inhibitors, as well as structural analogues and derivates thereof.

4. The method according to claim 1 wherein said peritoneal sample is fluid from the peritoneal space or from a peritoneal effluent of an individual undergoing peritoneal dialysis treatment or tissue from the peritoneum.

5. The method according to claim 1 wherein at least one additional study is undertaken prior to the step of administering to determine an amount of any one or more of the following in the peritoneal sample relative to said control sample:
(c) V$\delta$2$^+$ T cells expressing HLA-DR;
(d) TNF-$\alpha$;
(e) IL-1$\beta$; and/or
(f) monocytes within the peritoneal leukocyte population expressing CD86; and
where the amount of any one or more of (c)-(e) is increased relative to the amount of same in said control or in the case of (f) is decreased relative to the amount of same in said control, concluding that the individual from whom the peritoneal sample has been taken has a Gram-negative bacterial infection.

6. The method according to claim 5 wherein said method is performed using steps a-b and any one or more of steps (c)-(f) including any combination thereof.

* * * * *